United States Patent [19]

Yamamoto et al.

[11] Patent Number: 4,916,720
[45] Date of Patent: Apr. 10, 1990

[54] X-RAY ANALYZER

[75] Inventors: Naoki Yamamoto, Saitama; Yukio Takano, Tokyo; Yoshinori Hosokawa, Tsuzuki; Kenji Yoshino, Kyoto, all of Japan

[73] Assignees: Horiba, Ltd., Kyoto; Hitachi, Ltd., Tokyo, both of Japan

[21] Appl. No.: 271,534

[22] Filed: Nov. 15, 1988

[30] Foreign Application Priority Data

Nov. 27, 1987 [JP] Japan .................................. 62-297754

[51] Int. Cl.⁴ ............................................ G01N 23/20
[52] U.S. Cl. ........................................ 378/81; 378/44; 378/46; 378/72
[58] Field of Search ........................ 378/44, 46, 49, 81, 378/90, 86, 21, 72, 73, 77, 79

[56] References Cited

U.S. PATENT DOCUMENTS

| 3,344,274 | 9/1967 | Ashby et al. | 378/46 |
| 3,440,419 | 4/1969 | Das Gupta et al. | 378/46 |
| 3,903,414 | 9/1975 | Herbstein et al. | 378/46 |
| 4,263,510 | 4/1987 | Ciccarelli et al. | 378/46 |

Primary Examiner—Carolyn E. Fields
Assistant Examiner—David P. Porta
Attorney, Agent, or Firm—Price, Gess & Ubell

[57] ABSTRACT

An X-ray analyzer for performing both X-ray fluorescence and X-ray diffraction analysis is provided with an X-ray source, an X-ray guide tube for collimating X-rays from the source, a vacuum tank in which the guide tube is partially disposed, a rotatable sample table for holding a sample adjacent the guide tube, and an X-ray detector movable away from and towards the sample table, and also rotatable independently of the sample table.

14 Claims, 3 Drawing Sheets

X-RAY ANALYZER

DETAILED DESCRIPTION OF THE INVENTION

1. Field of the Invention

The present invention relates to an X-ray analyzer, and in particular to an X-ray analyzer for conducting an X-ray fluorescence analysis and an X-ray diffraction method.

2. Prior Art

A method in which a pinhole of a pinhole type collimator is minute-sized, or a method by an X-ray guide tube utilizing a total reflection of X-rays on an inner wall of a fine glass tube has been proposed for the X-ray diffraction of a minute crystal [Bulletin of Japanese Society of Metals, 24, No. 11, pp. 939–945 (1985)]. According to the latter, X-rays are guided far away by means of the fine glass tube and high brilliancy by minute-sized X-rays and the collection of X-rays is sought to be obtained. And, a paraboloid of revolution collection type X-ray guide tube or a ellipsoid of revolution spheroid type X-ray guide tube has been proposed by simulation using a computer.

On the other hand, no X-ray fluorescence analyzer capable of analyzing a minute crystal has been proposed.

Problems to be Solved by the Invention

It has never been taken into consideration in the X-ray diffractometer using the above described pinhole type collimator that the brilliancy of the X-rays reaching the sample is lowered. For that reason, it is difficult to dispose an X-ray incident side end of the collimator adjacent to a focus of a target, which is the X-ray source; only a part of the X-rays radially emitted from an X-ray target are incident upon the collimator; the X-rays emitted from the pinhole are radially diverged; and the irradiation range on the sample is unable to converge. Accordingly, a problem has occurred in that it is difficult to conduct X-ray diffraction of a minute crystal and a minute range.

In addition, in the case where a fine glass tube is used, a problem has obviously occurred in that even though an X-ray guide tube made of glass is produced on the basis of said simulation and the convergency o the X-rays is evaluated, the X-rays can not be collected as in the simulation.

In addition, in either of the above described cases, the measurement has been conducted in air and the X-ray fluorescence analysis has never been taken into consideration. Accordingly, a problem has occurred in that the X-ray diffraction and the X-ray fluorescence analysis can not be conducted by means of the same apparatus.

Thus, it is an object of the present invention to provide an X-ray analyzer capable of conducting both the X-ray diffraction and the X-ray fluorescence analysis of a minute part.

Measures for Solving the Problems

The above described object can be achieved by an X-ray analyzer, comprising an X-ray source, an X-ray guide tube for collecting X-rays emitted from said X-ray source, a sample table disposed in the vicinity of an end of said X-ray guide tube for placing a sample to be subjected to the application of the above described X-rays thereon and an X-ray detector, whereby X-ray fluorescence analysis and X-ray diffraction are both conducted.

According to the X-ray analyzer of the present invention, the energy dispersion type X-ray diffraction, the wavelength dispersion type X-ray diffraction and the X-ray fluorescence analysis can be conducted by one apparatus. In the case where it is necessary to detect low-energy fluorescent X-rays, it is necessary to dispose the sample table and the X-ray detector in the same one vacuum tank and keep an inside of the X-ray guide tube under vacuum. In addition, it is preferable that the above described vacuum tank and the inside of the X-ray guide tube are continuously vacuumed. The low-energy fluorescent X-rays are attenuated so as not to arrive at the detector in air.

In addition, it is preferable that the sample table and the X-ray detector are adapted to be coaxially and independently rotatable. In the X-ray fluorescence analysis, in order to efficiently detect weak fluorescent X-rays, it is preferable that the X-ray detector gets as near to the sample as possible while in the X-ray diffraction, in particular the wavelength dispersion type X-ray diffraction, it is preferable that a wavelength of the X-rays is fixed, the sample and the detector being rotated to measure a diffraction angle, at which the peak appears under the conditions meeting the diffraction condition of the Bragg equation, and it is preferable that the X-ray detector is disposed apart from the sample so as to make the separation of the diffraction angle easy. Accordingly, it is preferable that the X-ray detector is adapted to be movable in the radial direction of the above described rotation.

It is preferable that the sample table is movable independently in at least two axial directions of the rectangular coordinate system, and rotatable with a direction meeting at right angles with an axis of rotation for rotating the sample table as an axis so that the sample surface may be inclined. Such a rotating mechanism can be used for the evaluation of the anisotropy of stress in the measurement of an internal stress by the X-ray diffraction method.

In addition, it is preferable that means for heating the sample is provided. For example, the sample table is provided with a resistance heater. Such heating means can be used for the observation of stress and reaction process.

With the X-ray analyzer according to the present invention, the X-ray fluorescence analysis and the energy dispersion type X-ray diffraction method can be conducted in the same apparatus, so that for example the energy value of the diffraction peak from the desired sample can be determined from the energy value of the fluorescent X-rays. In addition, the diffraction peak energy value can be determined from the energy value of the characteristic X-rays of the material of the X-ray source detected by the elastic scattering or by using it together with the energy value of the fluorescent X-ray energy value.

In addition, for example the wavelength dispersion type X-ray diffraction method can be conducted by determining the angle of rotation of the sample table and the detector relative to the incident X-ray bundle from the energy value obtained by the above described method and correcting the angle of the rotating system in the apparatus or using this corrected angle of rotation as the relative angle of rotation of the sample table and the detector.

With the X-ray analyzer according to the present invention, the X-ray beams are highly parallel to each other, so that it is easy to set the conditions for the total reflection of the beams incident upon the sample, whereby for example the so-called total reflection X-ray fluorescence analysis becomes possible. Under these conditions, the X-rays hardly arrive at the detector arranged so as to turn in the direction meeting at almost right angles with the sample surface, whereby a S/N ratio in the detection of the fluorescent X-rays is remarkably improved.

1—X-ray apparatus; 2—X-ray guide tube; 3—Goniometer; 4—sample table; 5—Sample chamber; 6—Detector; 7—Laser source; 8—Television camera; 9—Monitor; 10—Scintillation counter; 11—Mirror; 12—Evacuating system; 22—Focus; 23—X-ray divergency-suppressing range; 24—X-ray transmission range; 25—Focus; 26—X-ray.

Next, one preferred embodiment of the X-ray guide tube used in the present invention is described.

Figure 4A:
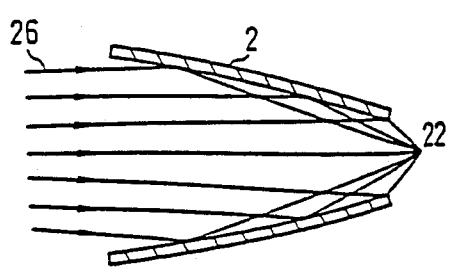
FIGS. 4, 5 are a partial sectional view showing one preferred embodiment of an X-ray guide tube.
Figure 4B:
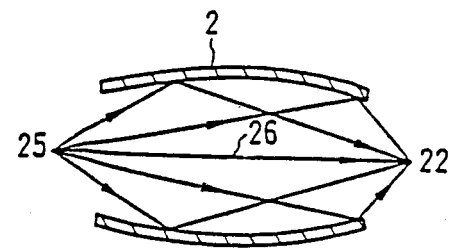

The conventional X-ray guide tube, which has been proposed by said simulation, as shown in FIGS. 4(a), (b), collects the X-rays 26 incident upon the X-ray guide tube 2 on each focus 22 by the use of the total reflection on the inner wall thereof to obtain minute and highly brilliant irradiated X-ray beams. However, when a photographic film is brought into direct contact with the emitting end of the paraboloid of revolution collection type X-ray guide tube made of glass having an inside diameter of 15 microns and an outside diameter of of 1 mm, with the X-rays being emitted from the incident end of the tube and the photosensitive spot on the film being measured, the beams are expanded to 73 microns, about 5 times the actual diameter of the opening. In addition, the X-ray beams are expanded to 410 microns in diameter at a position of 20 mm from the emitting end which is a focal position of the tube.

Figure 4C:
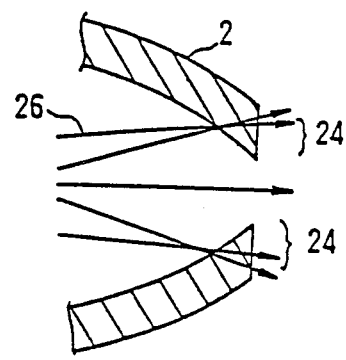

It seems to be that the reason why the inside diameter at the emitting end is remarkably different from the diameter of the X-rays at the end portion in the above described manner is that the X-rays incident upon the inner wall in the vicinity of the emitting end at the high angle of the critical angle of total reflection transmit the inside of the tube wall to be emitted outside, whereby the diameter of the X-ray beams is substantially expanded more than the inside diameter of the end portion, as shown in FIG. 4(c).

Figure 5A:
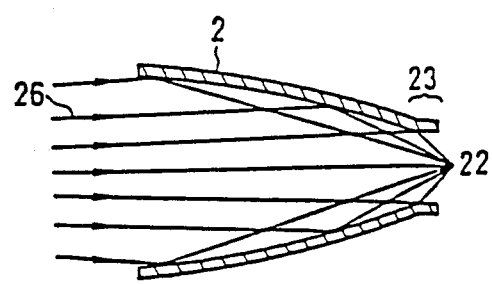
Figure 5B:
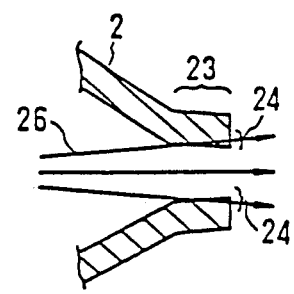

Accordingly, it is preferable to select the construction so that the X-rays incident upon the inner wall of the tube at the high angle of the critical angle of total reflection may not substantially leak in the emitting direction in the end portion range on the X-ray-emitting side of the X-ray guide tube. For example, it is preferable that the wall-thickness of the tube in the end portion range is increased in comparison with that of other parts or the change of inside diameter in the end portion range is eased in comparison with that in other ranges or made parallel to that in other ranges, as shown in FIGS. 5(a), (b). In this case, a small part of the X-ray transmission range 24 may remain in the end portion range, as shown in FIG. 5(b).

The use of such an X-ray guide tube leads to the possibility of efficiently guiding the X-rays from the X-ray source to the end portion of the tube. In addition, since the construction capable of preventing the X-rays from leaking from the tube wall in the end portion on the X-ray emitting side is adopted, minute and highly brilliant X-ray beams can be obtained. Also the parallel X-ray beams of the same extent as the synchrotron-emitted light can be obtained.

In addition, such a guide tube can be used in the usual X-ray analyzer.

Operation

Since the emitting end of the X-ray guide tube for guiding the X-rays is disposed in the vicinity of the target of the X-ray source, the X-rays, which have been divergently emitted from the target focus, can be efficiently taken in the X-ray guide tube. In addition, the end portion on the emitting side of the X-ray guide tube can be disposed in the vicinity of the sample and the X-rays emitted from the guide tube pass through the tube with total reflection to reduce the divergence. Thus, the minute X-ray beams having the high brilliancy and parallelism or minutely converged can be applied to the minute portion of the sample.

Preferred Embodiments

Figure 1:
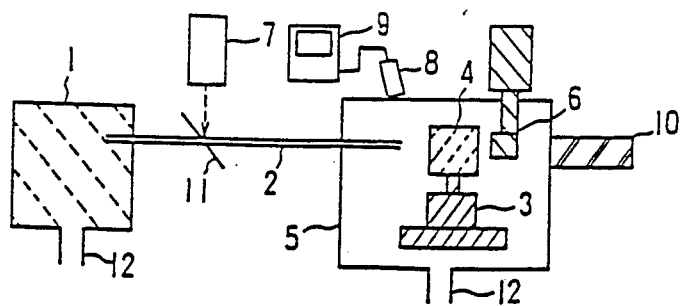
FIG. 1 is a block diagram showing one preferred embodiment of the basic construction according to the present invention.

The preferred embodiments of the present invention will be below described with reference to FIG. 1.

EXAMPLE 1

Figure 2:
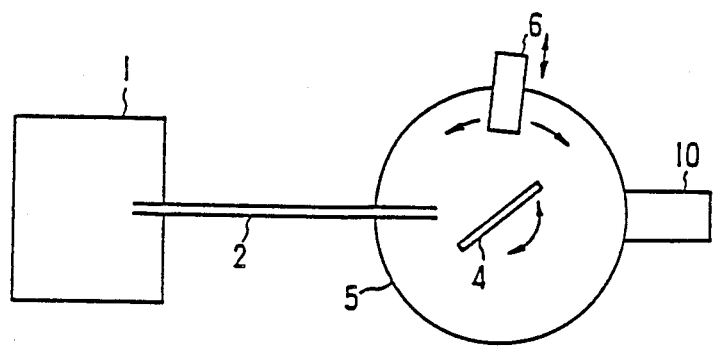
FIG. 2 is an upside view showing an arrangement of parts in one preferred embodiment of the present invention.
Figure 3:
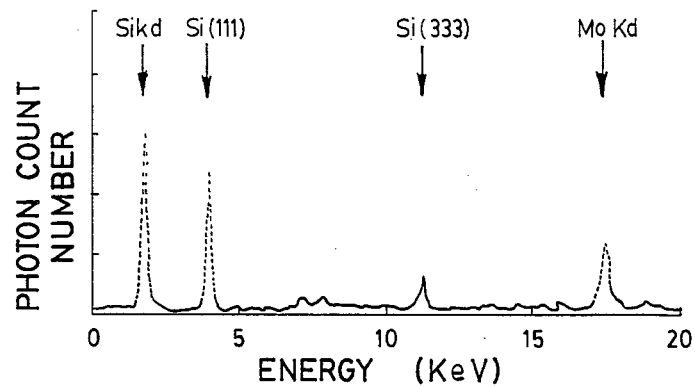
FIG. 3 is a diagram showing an energy spectrum of the fluorescent X-rays and the diffraction rays in EXAMPLE 1.

In the present EXAMPLE, in order to obtain the highly brilliant X-rays, a fine focus rotary pair of cathode type X ray apparatus (60 kV, 300 mA) 1 was used. A thin glass tube having an inside diameter at an incident end of 100 microns, an inside diameter at an emitting end on a sample side of 3 microns and a length of 60 cm was used as the X-ray guide tube 2 for guiding the X-ray bundle from the X-ray source to the sample. The opened end of the X-ray guide tube 2 was installed at a distance of about 1 cm from the X-ray target focus and the other end of the X-ray guide tube was installed at a distance of about 1 cm from the sample table 4 mounted on the goniometer 3. The X-ray source, the X-ray guide tube and the sample chamber 5 were connected in this order and the insides thereof were evacuated. Diffraction X-rays and fluorescent X-rays were detected by a Li-doped Si semiconductor detector 6 having a large area of about 100 mm$^2$. The position of the X-ray incident upon the sample was observed by means of a monitor 9 by guiding the laser beam emitted from a laser light source 7 so as to be parallel to and coaxial with the X-ray guide tube 2 and photographing a laser spot incident upon the sample by means of a television camera 8. The sample table 4 and the detector 6 were adapted to be coaxially and independently rotated. The goniometer 3 for moving the sample table was adapted to be rotated around X, Y and Z axes of the rectangular coordinates, rotated so as to tilt the sample table, and rotated so as to rotate the sample in a plane in addition to the above described rotation. In addition, the detector 6 was adapted to be moved also in the radial direction of rotation (FIG. 2). The reason for the above described construction is that in the X-ray fluorescence analysis the detector is approached to the sample as far as possible to efficiently detect weak fluorescent X-rays while in the X-ray diffraction method the detector is disposed apart from the sample to make the separation of the diffraction angle easy in order to make not only the energy dispersion type X-ray diffraction method but also the wavelength dispersion type X-ray diffraction method (the X-ray wavelength is fixed, the sample and the detector being rotated, and the diffraction angle, at which the peak appears under the conditions meeting the diffraction conditions of the Bragg equation being measured) possible. The sample table 4 was adapted to be heated up to 1,000° C. by means of a resistance heater. In order to confirm the performance of the apparatus according to the present invention, the divergence of the X-ray beams from the end portion on the emitting side of the X-ray guide tube at a time, when a Mo target was used as the X-ray source, was measured by means of a photographic dry plate. It was confirmed that a spot having a diameter of about 4 to 5 microns was observed on the end portion on the emitting side and a spot having a diameter of 7 to 8 microns on the sample table, the divergence angle being $10^{-3}$ radians or less, and the X-ray beams remarkably superior in parallelity and equivalent to the X-rays obtained by the light emitted from the synchrotron being obtained. Besides, the brilliancy of the X-ray beam on the sample table exhibited a value higher than that obtained when a pinhole type collimator having a diameter of 3 microns was used (a simulation value by the computer) by about 3 figures. FIG. 3 shows the results of measurement of the fluorescent X-rays and the energy dispersion type diffraction peak from a range having a diameter of about 7 to 8 microns of a Si (111) single crystal at room temperature. As shown in the drawing, also the K$\alpha$ line of Mo incident upon the detector by the elastic scattering from the Mo target of the X-ray source was observed in addition to the fluorescent X-rays of Si. In the case where the diffraction peak energy was determined using both the fluorescent X-rays of Si and the K$\alpha$ line of Mo, even the diffraction peak in the high-energy range could be determined in high accuracy In addition, the Gaussian fitting of energy spectrum was applied in the determination of the energy value.

EXAMPLE 2

The same construction as in EXAMPLE 1 except that the X-ray apparatus 1 and the system comprising the X-ray guide tube 2 and the sample chamber 5 were adapted to be independent to each other by adhering a Be thin plate to an end portion on an incident side of the X-ray guide tube 2 for passing X-rays therethrough to evacuate them by means of separate exhaust apparatus was adopted. In EXAMPLE 1, since the X-ray guide tube was connected with the X-ray source, the vibration generated during the time when the rotating pair of cathodes were rotated was transmitted to the X-ray guide tube, whereby also the end portion on the emitting side of the X-ray guide tube was vibrated which would be apt to expand the irradiation range on the sample. In the present EXAMPLE, since the X-ray guide tube is not brought into contact with the X-ray source system, the vibration of the rotating cathode portion has no influence to improve the X-ray irradiation range on the sample until 6 to 7 microns in diameter.

EXAMPLE 3

In the present EXAMPLE the X-ray fluorescence analysis was improved in sensitivity by the use of the apparatus having the same construction as in EXAMPLE 1. As above described, the X-ray beams emitted from the X-ray guide tube are remarkably high in parallelity. The present EXAMPLE is an example of the highly sensitive X-ray fluorescence analysis using this parallelity. Patterns formed of tungsten (W) having surface areas of 1 micron$^2$, 0.64 micron$^2$ and 0.25 micron$^2$ were formed on the Si substrate to produce samples having a thickness W of 500, 100 and 50 nm, respectively. Provided that a density of W is 19.3 g/cm$^3$, a weight of the W pattern having a surface area of 1 micron$^2$ and a thickness of 500 nm amounts to about 9.7 pg and that pattern having a surface area of 0.25 micron$^2$ and a thickness of 50 nm amounts to 0.24 pg. The rotating pair of cathodes type Mo target X-ray source was used to generate X-rays at 60 kV and 300 mA and emit them from the X-ray guide tube. An incident angle of the X-rays upon the sample was set at 60°. In this case, the fluorescent X-rays of W could be detected until the pattern of 2.4 pg. The patterns having a weight of 2.4 pg or less could not be detected due to noises resulting from the incident X-rays. On the other hand, the position, where the X-rays are incident upon the sample, was determined by means of a scintillation counter 10 shown in FIG. 1 so that the conditions of total reflection may hold good and a semiconductor detector was disposed close to the surface of the Si substrate as far as possible in a direction meeting at right angles with the surface of the Si substrate to conduct the X-ray fluorescence analysis in the same manner. In this case, the background noises resulting from the incident X-rays were reduced and the fluorescent X-rays of an infinitesimal quantity of tungsten of 0.48 pg could be detected on account of the effect of the disposition of the detector close to the sample.

EXAMPLE 4

In the present EXAMPLE the construction of the X-ray guide tube was investigated. At first, a soda glass tube having an inside diameter of 1 mm and an outside diameter of 10 mm was drawn with controlling a temperature of locally heating it and a drawing speed to produce a paraboloid of revolution collection type X-ray guide tube having an inside diameter on the incident side of the X-rays of 90 microns, an inside diameter at the end portion on the emitting side of 5 microns and a focal distance positioned at a point of 20 mm from the end portion. This was adopted as the basic construction. The construction of this X-ray guide tube is shown in FIG. 4(a). Next, after the glass tube was drawn under the same conditions as above described the drawing speed was rapidly increased at a point in time when the diameter at the end portion amounted to 5 microns to add a parallel tube portion 23 of about 2 mm to an end portion of the paraboloid of revolution, as shown in FIG. 5(a). An inside diameter of the end portion on the emitting side of this parallel tube-like X-ray guide tube was set at about 5 microns. The divergence of the X-ray beams of these two pieces of X-ray guide tube was measured using a photographic film. The former construction diverged the beam until a diameter of 23 microns at the end portion on the emitting side and 120 microns at the focal portion. On the contrary, the latter construction diverged the beam until a diameter of merely 7 microns at the end portion of the guide tube and 8 microns at the focal portion. That is to say, with the latter construction, the divergence of the X-rays could be suppressed, the collection efficiency being improved, and the minute beam being obtained. In addition, it was confirmed from the measurement of the brilliancy of the X-ray beam at the focal portion that the latter construction exhibited a brilliancy higher than that of the former construction by about 1.5 figures.

In addition, although a soda glass was used as the X-ray guide tube in the present EXAMPLE, it was found that the convergency of the X-rays could be remarkably improved also in the case where the X-ray guide tube was formed of other kinds of glass, such as pyrex glass and lead glass, and metals, such as molybdenum.

Effects of the Invention

According to the present invention, the minute X-ray beam showing the high brilliancy and parallelity or the minutely converged minute X-ray beam having a diameter of several microns can be obtained, whereby the X-ray diffraction method and the X-ray fluorescence analysis for a minute range of several microns to several ten microns level, which have been seemed to be difficult to achieve, become possible. In addition, the X-ray fluorescence analysis, the energy dispersion type X-ray diffraction method and the wavelength dispersion type X-ray diffraction

What is claimed is:

1. An X-ray analyzer comprising:
   an X-ray source;
   an X-ray guide tube for collecting X-rays emitted from said X-ray source;
   a sample table disposed in the vicinity of an end of said X-ray guide tube for supporting a sample to be subjected to the application of the abovedescribed X-rays, and
   an X-ray detector, said sample table and said X ray detector being coaxially and independently rotatable and said X-ray detector being further radially movable relative to said sample table to enable detection of the X-rays relative to a sample.

2. The X-ray analyzer of claim 1 further including a vacuum housing member for maintaining a vacuum, said sample table and said X-ray detector are positioned within the vacuum housing member and the inside of said X-ray guide tube is opened into said vacuum housing member.

3. The X-ray analyzer of claim 1 wherein one end of the guide tube is smaller than the other end.

4. The X-ray analyzer of claim 1 wherein said guide tube has a curved inner wall.

5. The X-ray analyzer of claim 1 wherein said sample table is movable in at least two axial directions of rectangular coordinates.

6. The X-ray analyzer of claim 1 wherein an inner diameter of said guide tube is reduced at an emitting end within a critical angle of reflection of the X-rays to prevent leakage of X-rays from said guide tube.

7. The X-ray analyzer of claim 2 wherein an inner diameter of said guide tube is reduced at an emitting end within a critical angle of reflection of the X-rays to prevent leakage of X-rays from said guide tube.

8. The X-ray analyzer of claim 3 wherein said guide tube has a curved inner wall adjacent its opening, near said sample table, of a configuration to focus X-rays on a sample.

9. A system for conducting both X-ray fluorescence analysis and X-ray diffraction analysis, comprising:
   a vacuumable environment;
   a guide means for guiding X-rays towards a sample, said guide means being disposed in said environment;
   holding means for holding said sample in said environment while said sample is impinged by said X-rays, said holding means being rotatable, and
   detection means for detecting X-rays from said sample, said detection means being translatable and rotatable independent of said holding means, said detection means is translatable towards and away from said sample.

10. The system according to claim 9 wherein said guide means includes an outlet end having a construction such that X-rays incident upon an inner wall of said guide means at a high angle of a critical angle of total reflection will not substantially leak in an emitting direction.

11. The system according to claim 9 wherein said detection means is disposed in said environment.

12. The system according to claim 9 wherein said holding means is rotatable about two axial directions of a rectangular coordinate system.

13. The system according to claim 9 wherein said guide tube has a curved inner wall.

14. The system according to claim 9 wherein said guide tube has a curved inner wall, adjacent its emitting end, of a configuration to focus X-rays on said holding means.

* * * * *